(12) United States Patent
Womack et al.

(10) Patent No.: US 6,534,265 B1
(45) Date of Patent: Mar. 18, 2003

(54) ORYZACYSTATIN-I APPLICATIONS AND METHODS

(75) Inventors: James S. Womack, Albuquerque, NM (US); Jennifer J. Randall, Las Cruces, NM (US); John D. Kemp, Las Cruces, NM (US)

(73) Assignee: New Mexico State University Technology Transfer Corporation, Las Cruces, NM (US)

( * ) Notice: Subject to any disclaimer, the term of this patent is extended or adjusted under 35 U.S.C. 154(b) by 0 days.

(21) Appl. No.: 09/504,633

(22) Filed: Feb. 15, 2000

Related U.S. Application Data

(60) Provisional application No. 60/120,424, filed on Feb. 16, 1999.

(51) Int. Cl.[7] ................................................. C12Q 1/68
(52) U.S. Cl. ............................ 435/6; 435/5; 435/91.1; 435/91.2; 435/252.2; 435/252.3; 435/252.33; 435/320.1; 435/419; 435/440; 530/350; 530/351; 536/23.2; 536/23.6; 800/27.8; 800/302
(58) Field of Search ............................... 435/5, 6, 91.1, 435/912, 252.2, 252.3, 252.33, 320.1, 419, 440; 530/350, 351; 536/23.2, 23.6; 800/27.8, 302

(56) References Cited

U.S. PATENT DOCUMENTS

| | | | |
|---|---|---|---|
| 5,212,297 A | | 5/1993 | Colella et al. |
| 5,494,813 A | | 2/1996 | Hepher et al. |
| 5,863,775 A | | 1/1999 | Atkinson et al. |
| 5,919,658 A | | 7/1999 | Ni |
| 5,990,390 A | | 11/1999 | Lundquist |
| 6,013,863 A | | 1/2000 | Lundquist |
| 6,054,637 A | * | 4/2000 | Boller et al. ................. 800/298 |

OTHER PUBLICATIONS

Masoud et al. Plant Molecular Biology. vol. 21, pp. 655–663, 1993.*
Abe et al., Purification of a cysteine proteinase inhibitor from rice, *Oryza sativa. Agric Biol Chem* 49:3349–3350 (1985)).
Abe et al., Molecular cloning of a cysteine proteinase inhibitor of rice (oryzacystatin). *J Biol Chem* 262: 16793–16797 (1987).
Abe et al., Structural Organization of the Gene encoding Corn Cystatin, *Biosci Biotech Biochem* 60 (7):1173–1175 (1996).
Abe et al., The NH$_2$–teminal 21 Amino Acid Residues are not Essential for the Papain–inhibitory Activity of Oryzacystatin, a Member of the Cystatin Superfamily,*J Biol Chem* vol. 263, No. 16:7655–7659 (1988).

Ahman et al., Sequence analysis and regulation of a gene encoding a cuticle–degrading serine protease from the nematophagus fungus *Arthrobotrys oligospor. Microbiology* 142:1605–1616 (1996).
Chrispeels, Sorting of proteins in the secretory system. *Annu Rev Plant Physiol Plant Mol Biol* 42:21–53 (1991).
Horsch et al., A simple and general method for transforming genes into plants. *Science* 227:1229–1231 (Mar. 8, 1985).
Horsch, et al., A Simple and General Method for Transferring Genes into Plants, *Science* 227 (1985) pp. 1229–1231.
Hosoyama, et al., Introduction of a chimeric gene encoding an oryzacystatin–β–glucuronidase fusion protein into rice protoplasts and regeneration of transformed plants, *Plant Cell Reports* 15:174–177 (1995).
Irie et al., Transgenic rice established to express corn cystatin exhibits strong inhibitory activity against insect gut proteinases. *Plant Mol Biol* 30:149–157 (1996).
Kikuta–Oshima et al., Abst. 340, *ASPP*, p. 86 (1998).
Klypina et al., A chimeric oryzacystatin–I/*Bacillus thruingiensis* Cry3A gene which is expressed at high levels in transgenic plants, Abst. 330, *ASPP* p. 84 (1998).
Kondo et al. Cloning and sequence analysis of the genomic DNA fragment encoding oryzacystatin *Gene* 81:259–265 (1989).
Kondo et al., Two Distinct Cystatin Species in Rice Seeds with Different specificities against Cysteine Proteinases, *J Biol Chem* vol. 265, No. 26:15832–15837 (1990).
Laemmli, Cleavage of Structural Proteins during the Assembly of the Head of Bacteriophage T4, *Nature* 227:680–685 (1970).
Li et al., Direct Submission to GenBank, Accession # 1076759, PID g1076759.
Masoud et al., Expression of a cysteine proteinase inhibitor (oryzacystatin–I) in transgenic tobacco plants. *Plant Mol Biol* 21:655–663 (1993).
Richter et al., Characterization and genomic organization of a highly expressed late nodulin gene subfamily in Soybeans. *Mol Gen Genet* 229:445–452 (1991).
Rogers et al., Improved Vectors for Plant Transformation: Expression Cassette Vectors and New Selectable Markers, *Methods and Enzymology* 153:253–277 (1987).
Urwin et al., Enhanced transgenic plant resistance to nematodes by dual proteinase inhibitor constructs. *Planta* 204:472–479 (1998).

(List continued on next page.)

*Primary Examiner*—Stephanie W. Zitomer
*Assistant Examiner*—Janell E. Taylor
(74) *Attorney, Agent, or Firm*—Stephen A. Slusher; Deborah A. Peacock

(57) ABSTRACT

A nucleic acid sequence encoding for oryzacystatin-I peptides and a signal peptide therefore is provided. The oryzacystatin-I peptide is approximately 12.6 kDa, and is approximately twelve amino acid residues longer than previously described oryzacystatin-I peptides. The nucleic acid sequences may be cloned into vectors, and used to transform plants conferring resistance to plant pests, including insects and nematodes, that utilize cysteine proteases, and to viruses with processing mechanisms involving cysteine proteases.

12 Claims, 5 Drawing Sheets

OTHER PUBLICATIONS

Urwin et al., Engineered Oryzacystatin–1 Expressed in Transgenic Hairy Roots Confers Resistance to *Globodera pallida, Plant J* 8:121–131 (1995).

Abrahamson et al., Molecular cloning and sequence analysis of cDNA coding for the Precursor of the human cysteine proteinase inhibitor cystatin C, *FEBS Lett* 216(2):229–233 (1987).

Kondo, et al., GenBank Accession No. M29259, protein ID AAA33912.1.

Womack, et al., GenBank accession AF16378; PlantGene Register database PGR 99–175.

Gutierrez–Compos, R., et al., "The Use of Cysteine Proteinase Inhibitors to Engineer Resistance Against Potyviruses in Transsgenic Tobacco Plants," *Nature Biotechnology*, vol. 17, pp 1223–1226 (Dec. 1999).

* cited by examiner

```
1               M   R   K   Y   R   V   A   G
1       aga tct ATG CGG AAA TAT CGA GTC GCC GGA
        BglII 9               L   V   A   A   L   L   V   L   H   S
31              TTG GTA GCC GCC CTG CTC GTG CTG CAT TCG 19              L   A   T   P   S   A   Q   A   E   A
61              CTA GCC ACG CCG TCC GCT CAG GCC GAG GCG 29              H   R   A   G   G   E   G   E   E   K
91              CAT CGC GCA GGG GGA GAA GGG GAG GAG AAG 39              M   S   S   D   G   G   P   V   L   G
121             ATG TCG AGC GAC GGA GGG CCG GTG CTT GGC 49              G   V   E   P   V   G   N   E   N   D
151             GGC GTC GAG CCG GTG GGG AAC GAG AAC GAC 59              L   H   L   V   D
181             CTC CAC CTC gtc gac
                                SalI
```

Fig. 1

SEQUENCE LISTING

```
<160> NUMBER OF SEQ ID NOS: 7

<210> SEQ ID NO 1
<211> LENGTH: 37
<212> TYPE: PRT
<213> ORGANISM: Oryza sativa
<300> PUBLICATION INFORMATION:
<302> TITLE: Oryzacystatin-I has a signal peptide (Accession No.
      AF164378) (PGR99-175)
<303> JOURNAL: Plant Physiol.
<304> VOLUME: 121
<305> ISSUE: 4
<306> PAGES: 1383-
<307> DATE: 1999
<308> DATABASE ACCESSION NUMBER: AF164378 (PGR99-175)
<309> DATABASE ENTRY DATE: 1999-12-30
<313> RELEVANT RESIDUES: 3 TO 4

<400> SEQUENCE: 1

Glu Ala His Arg Ala Gly Gly Glu Gly Glu Glu Lys Met Ser Ser Asp
```

```
                1               5              10              15
Gly Gly Pro Val Leu Gly Gly Val Glu Pro Val Gly Asn Glu Asn Asp
                    20              25              30

Leu His Leu Val Asp
        35

<210> SEQ ID NO 2
<211> LENGTH: 26
<212> TYPE: PRT
<213> ORGANISM: Oryza sativa
<220> FEATURE:
<221> NAME/KEY: SIGNAL
<222> LOCATION: (1)..(26)
<223> OTHER INFORMATION: OC-I signal peptide

<400> SEQUENCE: 2

Met Arg Lys Tyr Arg Val Ala Gly Leu Val Ala Ala Leu Leu Val Leu
 1               5                  10                  15

His Ser Leu Ala Thr Pro Ser Ala Gln Ala
            20                  25

<210> SEQ ID NO 3
<211> LENGTH: 189
<212> TYPE: DNA
<213> ORGANISM: Oryza sativa
<220> FEATURE:
<221> NAME/KEY: CDS
<222> LOCATION: (1)..(189)
<223> OTHER INFORMATION: SPOC-I; signal peptide/OC-I preprotein
<220> FEATURE:
<221> NAME/KEY: sig_peptide
<222> LOCATION: (1)..(78)
<223> OTHER INFORMATION: OC-I signal peptide coding sequence

<400> SEQUENCE: 3 atg cgg aaa tat cga gtc gcc gga ttg gta gcc gcc ctg ctc gtg ctg        48
Met Arg Lys Tyr Arg Val Ala Gly Leu Val Ala Ala Leu Leu Val Leu
 1               5                  10                  15 cat tcg cta gcc acg ccg tcc gct cag gcc gag gcg cat cgc gca ggg        96
His Ser Leu Ala Thr Pro Ser Ala Gln Ala Glu Ala His Arg Ala Gly
            20                  25                  30 gga gaa ggg gag gag aag atg tcg agc gac gga ggg ccg gtg ctt ggc       144
Gly Glu Gly Glu Glu Lys Met Ser Ser Asp Gly Gly Pro Val Leu Gly
        35                  40                  45 ggc gtc gag ccg gtg ggg aac gag aac gac ctc cac ctc gtc gac            189
Gly Val Glu Pro Val Gly Asn Glu Asn Asp Leu His Leu Val Asp
    50                  55                  60

<210> SEQ ID NO 4
<211> LENGTH: 63
<212> TYPE: PRT
<213> ORGANISM: Oryza sativa

<400> SEQUENCE: 4

Met Arg Lys Tyr Arg Val Ala Gly Leu Val Ala Ala Leu Leu Val Leu
 1               5                  10                  15

His Ser Leu Ala Thr Pro Ser Ala Gln Ala Glu Ala His Arg Ala Gly
            20                  25                  30

Gly Glu Gly Glu Glu Lys Met Ser Ser Asp Gly Gly Pro Val Leu Gly
        35                  40                  45

Gly Val Glu Pro Val Gly Asn Glu Asn Asp Leu His Leu Val Asp
    50                  55                  60
```

-continued

```
<210> SEQ ID NO 5
<211> LENGTH: 30
<212> TYPE: DNA
<213> ORGANISM: Oryza sativa
<220> FEATURE:
<221> NAME/KEY: primer_bind
<222> LOCATION: (1)..(30)
<223> OTHER INFORMATION: Primer sequence for OC-I signal peptide coding
      region; sense

<400> SEQUENCE: 5
cccagatcta tgcggaaata tcgagtcgcc                                        30

<210> SEQ ID NO 6
<211> LENGTH: 21
<212> TYPE: DNA
<213> ORGANISM: Oryza sativa
<220> FEATURE:
<221> NAME/KEY: primer_bind
<222> LOCATION: Complement((1))
<223> OTHER INFORMATION: Primer sequence for OC-I signal peptide coding
      region

<400> SEQUENCE: 6
gcgaggtcga cgaggtggag g                                                 21

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:Conserved
      sequence

<400> SEQUENCE: 7

Gln Val Val Ala Gly
 1               5
```

ORYZACYSTATIN-I APPLICATIONS AND METHODS

CROSS-REFERENCE TO RELATED APPLICATIONS

This application claims the benefit of the filing of U.S. Provisional Patent Application Serial No. 60/120,424, entitled "Signal Peptide for Oryzacystatin-I Targets Propeptide to ER", filed on Feb. 16, 1999, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. 95-34250-1413 awarded by the U.S. Department of Agriculture.

BACKGROUND OF THE INVENTION

1. Field of the Invention (Technical Field)

The present invention relates to a novel oryzacystatin protease inhibitor peptide, including a signal peptide component thereof, nucleic acid sequences encoding the protein and signal peptide, incorporation of the oryzacystatin protease inhibitor gene into the genome of a plant and the expression of the inhibitor gene in plants whereby such plants are less susceptible to insect and plant pest damage, and to damage caused by certain plant viruses. The invention is further directed to methods for producing the complete oryzacystatin protease inhibitor peptide, compositions containing the complete oryzacystatin protease inhibitor peptide for use as insecticidal agents, and the use of oryzacystatin protease inhibitor peptide for decreasing insect and virus damage to plants.

2. Background Art

There is significant interest in the use of materials and methods to control insect damage to commercially valuable crop plants that does not require the use of conventional chemical insecticides and chemical fumigation methods. One approach that has been studied employs the use of protease or peptidase inhibitors that are toxic to or substantially inhibit certain insects.

Proteases and peptidases are enzymes that hydrolyze the peptide bonds of proteins or peptides, respectively. These proteases or peptidases (collectively referred to as proteases) play a number of roles in biochemical regulation of organisms, including insects. For example, peptides are generated from proteins by the action of proteases in the gastrointestinal tract of organisms. Through use of these proteases, proteins are broken down into absorbable peptides or individual amino acids, thereby providing sustenance to the organism. Disruption of protease activity can thus have a significant adverse effect on the life cycle of organisms.

There are a number of mechanisms that regulate protease enzymatic activity; one of the most potent and direct mechanisms is through the use of protease inhibitors. Based on the catalytic mechanism employed, there are four classes of protease enzymes, of which one such class is cysteine or thiol proteases. Cysteine proteases are widely distributed, and occur in plants, animals, bacteria and a wide variety of microorganisms. These organisms include specifically plant and animal pests and parasites, as described generally in U.S. Pat. Nos. 5,494,813 and 5,863,775.

Cystatins are well known inhibitors of cysteine proteases. A wide variety of cystatin-type inhibitors have been documented, and these are naturally expressed in a wide variety of plants and animals as part of the regulatory scheme of proteolytic activity. Thus cystatins are naturally found in chickens, including egg whites, U.S. Pat. No. 5,212,297; humans, U.S. Pat. No. 5,919,658; rice and maize, U.S. Pat. No. 5,863,775; and a wide variety of other plants and animals.

Research on the use of cystatins as a means of crop pest control has grown due to the wide spectrum of activity these proteinacious inhibitors possess. The cloning of oryzacystatin-I (OC-I), one of the earliest characterized cystatins of plant origin (Abe et al., Purification of a cysteine proteinase inhibitor from rice, Oryza sativa. Agric Biol Chem 49: 3349–3350 (1985)), was first published over a decade ago (Abe et al., Molecular cloning of a cysteine proteinase inhibitor of rice (oryzacystatin). J Biol Chem 262: 16793–16797 (1987); GenBank accession M29259), with other plant cystatins quick to follow, including oryzacystatin-II (OC-II) (Kondo et al., Two distinct cystatin species in rice seeds with different specificities against cysteine proteinases. J Biol Chem 265: 15832–15837 (1990)), corn cystatin-I (CC-I), corn cystatin-II (CC-II) (Abe et al., Structural organization of the gene encoding corn cystatin. Biosci Biotech Biochem 60: 11731–1175 (1996)), and a cystatin from sorghum (Li et al., Direct Submission to GenBank, Accession # 1076759, PID g1076759). These cystatins share a high degree of similarity and contain a highly conserved sequence, Gln-Val-Val-Ala-Gly (SEQ ID NO: 7) believed to be the active region of the inhibitor responsible for binding cysteine proteases (Abe et al., The $NH_2$-terminal 21 amino acid residues are not essential for the papain-inhibitory activity of oryzacystatin, a member of the cystatin superfamily. J Biol Chem 263: 7655–7659 (1988)).

To date, the transformation of plants with OC-I cDNAs has resulted in low or inconsistent protein yields (Masoud et al., Expression of a cysteine proteinase inhibitor (oryzacystatin-I) in transgenic tobacco plants. Plant Mol Biol 21: 655–663 (1993); Irie et al., Transgenic rice established to express corn cystatin exhibits strong inhibitory activity against insect gut proteinases. Plant Mol Biol 30: 149–157 (1996)). There are reports that plants transformed with OC-I do not significantly hinder the growth of certain crop pests, such as the Coleoptera, *Phaedon cochleariae*, and may actually cause the pests (*Psylliodes chrysocephala* L. and *Ceutorhynchus assililis*) to thrive.

Low protein yields of OC-I occurred even when the cDNA was inserted back into the source plant, *Oryza sativa* L. japonica, for the purpose of enhancing the effectiveness of the innate OC-I against pests (Irie et al., supra). Thus it has not heretofore been possible to express consistent and high protein yields of OC-I using cDNA transformation methods with the heretofore-identified gene segments.

A variety of different methods have been attempted to employ transformation schemes that result in commercially and agriculturally viable expression of useful levels of OC-I. The earliest report was by Masoud et al. (Expression of a cysteine proteinase inhibitor (oryzacystatin-I) in transgentic tobacco plants. Plant Mol Biol 21: 655–663 (1993)). Attempts have been made to stabilize OC-I in plants through such approaches as engineering fusion proteins using genes from cowpea trypsin inhibitor (CPTI) (Urwin et al., Enhanced transgenic plant resistance to nematodes by dual proteinase inhibitor constructs. Planta 204: 472–479 (1998), beta-glucuronidase (Hosoyama et al., Introduction of a chimeric gene encoding an oryzacystatin-β-glucuronidase fusion protein into rice protoplasts and regeneration of transformed plants. *Plant Cell Reports* 15: 174–177 (1995)), *Bacillus thuringiensis* Cry 3A (Klypina et al., A chimeric oryzacystatin-I/*Bacillus thruingiensis* Cry3A gene which is expressed at high levels in transgenic plants, Abst. 330, *ASPP* p. 84 (1998)) and the 10 kDa zein seed storage protein from maize (Kikuta-Oshima et al., A 10 kDa zein/oryzacystatin-I protease inhibitor chimeric gene designed for the stabilization of proteins for the purpose of plant pest control is expressed in transgenic plants. Abst. 340, *ASPP*, p. 86 (1998)). Although these strategies seem to improve the stability of OC-I accumulation in transgenic plants, it is unclear whether the resulting fusion proteins retain any cystatin activity.

It has been heretofore universally known that oryzacystatins, unlike the maize cystatins, have no N-terminal leader sequences, and therefore probably remain cystostolic after translation. This assumption was based, in significant part, upon a protein produced by the OC-I gene reported by Abe et al. (1987) and Kondo et al. (Cloning and sequence analysis of the genomic DNA fragment encoding oryzacystatin. *Gene* 81: 259–265 (1989)).

Since its discovery, OC-I has been investigated for use as a crop pest deterrent primarily because of its function as an insect digestive system protease inhibitor (see, e.g., U.S. Pat. Nos. 5,863,775 and 5,494,813, Irie et al., supra.). The belief that OC-I is a cytosolic protein was considered important in the work of Urwin et al. (Engineered oryzacystatin-I expressed in transgenic having roots confers resistance to *Globodera pallida*. *Plant J* 8: 121–131 (1995)), since nematodes appear to feed only on the cytosol. This belief was supported by the report that OC-I did not appear to have a functional signal peptide (Abe et al. 1988, supra). Several groups have attempted to express the OC-I gene in plants expecting accumulation of OC-I to be sufficient for plant defense, but reproducible levels of accumulation remained elusive. Based on this disclosure of this invention, the instability of prior art OC-I There is also interest in the use of cysteine protease inhibitors to engineer resistance against viruses, including certain potyviruses. (Gutierrez-Campos et al., The use of cystein proteinase inhibitors to engineer resistance against potyviruses in transgenic tobacco plants. *Nature Biotech* 17: 1223–1226 (1999)). The processing mechanism of certain viruses, including all known potyviruses, involves the activity of cysteine proteases. Preliminary research has demonstrated that there is a correlation between the level of OC-I message and resistance against viruses with processing mechanisms involving cysteine proteases, such as tobacco etch virus and potato virus Y. Thus effective methods to induce high levels of OC-I expression in plants may afford significant protection against viruses with processing mechanisms involving cysteine proteases, as well as affording protection against plant pests, including insects and nematodes, which utilize cysteine proteases in endogenous metabolic pathways.

Thus there is a significant need for methods and reagents which will result in expression of consistent and high levels of OC-I in various plants, and which result in levels of OC-I expression which are effective for protection against both plant pests and viruses susceptible to cystatin inhibition.

SUMMARY OF THE INVENTION (DISCLOSURE OF THE INVENTION)

The invention includes an oryzacystatin-I protease inhibitor peptide that includes the amino acid sequence of SEQ ID NO: 1 and sequences that are functionally homologous with the amino acid sequence of SEQ ID NO: 1. It further includes an isolated pre-oryzacystatin-I peptide called SPOC-I that is characterized by the amino acid sequence of SEQ ID NO: 4 and sequences that are functionally homologous with the amino acid sequence of SEQ ID NO: 4. The invention includes a recombinant DNA molecule that includes a nucleic acid sequence encoding the amino acid sequence of SEQ ID NO: 4. The invention further includes transgenic plants that include a foreign nucleic acid sequence encoding the amino acid sequence of SEQ ID NO: 4 and sequences that are functionally homologous with the amino acid sequence of SEQ ID NO: 4.

The invention also includes a nucleic acid sequence encoding both a signal peptide for OC-I and an OC-I peptide. Transgenic plants that include a foreign nucleic acid sequence encoding both the signal peptide OC-I and the OC-I peptide are included within the invention. The nucleic acid sequence may be a recombinant DNA molecule. The recombinant DNA molecule may be characterized or described in that it is a vector. The invention includes protein, including purified peptide, which is derived from the expression of a nucleic acid sequence encoding both a signal peptide for OC-I and an OC-I peptide. In one embodiment, the nucleic acid sequence includes that set forth in SEQ ID NO: 3 and sequences functionally homologous with the sequence set forth in SEQ ID NO: 3. Host cells may be transformed with vectors that are recombinant DNA molecules encoding both a signal peptide for OC-I and an OC-I peptide. Representative host cells include maize, sweet corn, squash, melon, cucumber, sugarbeet, sunflower, rice, cotton, canola, sweet potato, bean, cowpea, tobacco, soybean and alfalfa cells.

In another embodiment, the invention includes a cystatin protease inhibitor peptide having an amino acid sequence extending from amino acid position 13 to 37 of SEQ ID NO: 1 and at least a portion of the sequence extending from amino acid position 1 to 12, and peptides that are functionally equivalent, such as peptides that have an amino acid sequences functionally homologous to amino acid position 13 to 37 of SEQ ID NO: 1 and that further contain at least a portion of the sequence extending from amino acid position 1 to 12. Also included are recombinant DNA molecules that include a nucleic acid sequence encoding a peptide having an amino acid sequence extending from amino acid position 13 to 37 of SEQ ID NO: 1 and at least a portion of the sequence extending from amino acid position 1 to 12, and peptides that are functionally equivalent. Transgenic plants that include a foreign nucleic acid sequence encoding a peptide having an amino acid sequence extending from amino acid position 13 to 37 of SEQ ID NO: 1 and at least a portion of the sequence extending from amino acid position 1 to 12, and peptides that are functionally equivalent are included within the invention.

The OC-I peptide of this invention may be an homogenous protease inhibitor OC-I peptide characterized by a molecular weight of about 12.6 kDa on an SDS PAGE with binding affinity to polyclonal antibodies to recombinant OC-I.

The invention further provides a method of combating insect pests which includes exposing pests to an insecticidally effective amount of an OC-I peptide, wherein the peptide is expressed in a plant or plant colonizing microorgranism as a result of genetic transformation by a nucleic acid sequence encoding both a signal peptide for OC-I and an OC-I peptide. The plant may be a maize, sweet corn, squash, melon, cucumber, sugarbeet, sunflower, rice, cotton, canola, sweet potato, bean, cowpea, tobacco, soybean or alfalfa plant.

The invention further provides a method of combating viruses with processing mechanisms involving cysteine proteases, which method includes exposing viruses to a viricidally effective amount of an OC-I peptide, wherein the peptide is expressed in a plant as a result of genetic transformation by a nucleic acid sequence encoding both a signal peptide for OC-I and an OC-I peptide. The plant may be a maize, sweet corn, squash, melon, cucumber, sugarbeet, sunflower, rice, cotton, canola, sweet potato, bean, cowpea, tobacco, soybean or alfalfa plant.

A primary object of the present invention is the expression of useful levels of OC-I in crop plants, including, but not limited to, crop plants in which OC-I is naturally expressed, such that the crop plant is effectively resistant to plant pests and viruses susceptible to cystatin inhibition.

Another object of the present invention is to provide the complete genomic DNA for OC-I, including that portion coding a signal peptide, such that transformed eukaryotic organisms express high levels of biologically active OC-I.

Another object of the present invention is to provide an OC-I peptide that is appropriately 12 residues larger than previously described, comprising the peptide sequence (utilizing conventional single letter codes) EAHRAGGE-GEEKMSSDGGPVLGGVEPVGNENDLHLVD (SEQ ID NO: 1), which peptide may be expressed in transformed organisms using genomic DNA.

A primary advantage of the present invention is that it provides heretofore unknown genomic DNA encoding for functional OC-I in transformed eukaryotic organisms, including a signal peptide for OC-I necessary for processing the encoded pre-protein into a mature and function form of OC-I.

Another advantage of the present invention is that it provides efficient and effective methods for producing functional OC-I.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 1 is the nucleic acid and DNA sequence of the 5'-end of the OC-I gene. Restriction sites used for recombination are shown in lowercase italics. The amino acid sequence (using single letter codes) is shown above the DNA sequence, with the start codon and signal peptide shown in bold. The previously known start codon is underlined (Met-39).

DESCRIPTION OF THE PREFERRED
EMBODIMENTS (BEST MODES FOR
CARRYING OUT THE INVENTION)

The present invention relates to a full-length cDNA clone that encodes for both a signal peptide for oryzacystatin-I (OC-I) (SEQ ID NO: 2) and the mature form of OC-I (SEQ ID NO: 1). Prior art cDNA clones did not encode for the signal peptide for OC-I (the OC-I pre-protein comprising the signal peptide and OC-I sequence of this invention is referred to as SPOC-I). Similarly, prior art cDNA clones, when utilized to express a form of OC-I, did not express the entire and mature form of OC-I, as OC-I is disclosed in this invention. The SPOC-I sequence of this invention is processed into the mature form of OC-I within the plant, presumably through microsomal membranes. The OC-I expressed by the cDNA clones of this invention, upon processing of the SPOC-I sequence, is approximately 12.6 kDa, and is approximately 12 amino acid residues larger than prior art described OC-I, including prior art OC-I produced using prior art cDNA clones.

The cDNA clones of this invention may be used to transform ornamental, crop or other plants, with such resulting plants having insect and virus resistance on expression of the resulting OC-I peptide. Such cDNA may be used to increase OC-I expression in plants naturally expressing OC-I, such as rice, or may be used to express OC-I in plants not naturally expressing OC-I.

A previously unidentified extension of an open reading frame (ORF) from the genomic DNA of Oryza sativa L. japonica encoding oryzacystatin-I (OC-I) (GenBank Accession No. M29259, protein ID AAA33912.1) is identified as a 5' gene segment coding for the OC-I signal peptide. The signal peptide presumably directs the SPOC-I pre-protein (GenBank accession AF164378; PlantGene Register database PGR 99-175) to the endoplasmic reticulum, where it is processed into the mature form of OC-I. The start codon of SPOC-I begins 114 bp upstream from the prior art start codon described for OC-I. The DNA sequence is shown at SEQ ID NO: 3, together with the corresponding SPOC-I amino acid sequence. The complete SPOC-I amino acid sequence is shown at SEQ ID NO: 4. A proteolytic site is identified within SPOC-I between Ala-26 and Glu-27, yielding the mature OC-I of this invention (SEQ ID NO: 1) approximately 12 residues larger than previously described.

Figure 4:
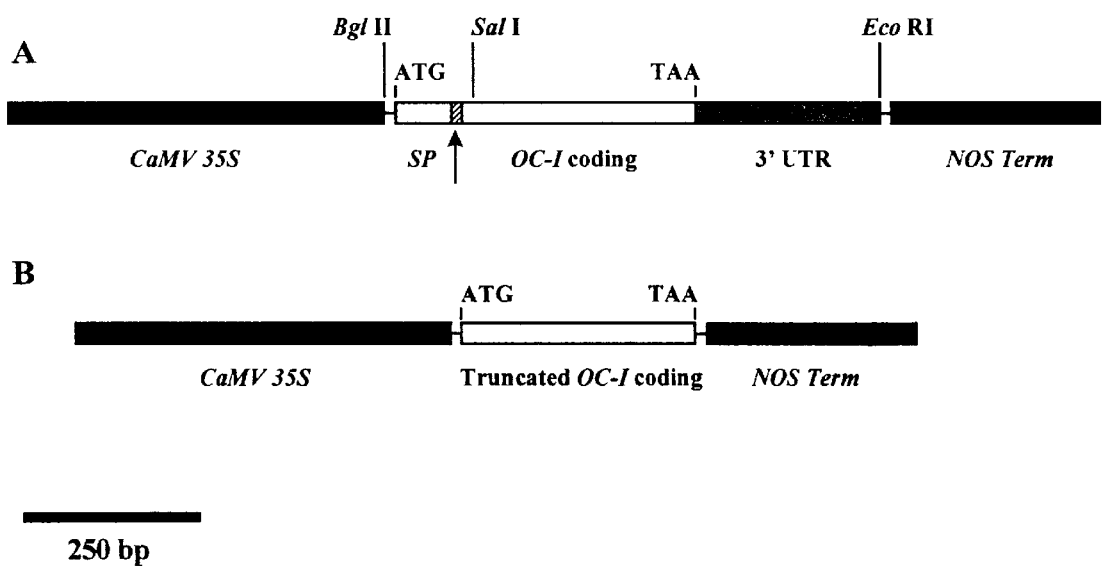
FIG. 4A describes a plasmid map of the OC-I gene construct of this invention, including the signal peptide coding sequence.
FIG. 4B describes a plasmid map of the prior art truncated OC-I coding sequence that does not code for the OC-I signal peptide.

FIG. 1 depicts the nucleic acid sequence of the 5' end of the SPOC-I gene, including OC1. Restriction sites used for recombination are shown in lowercase italics. The amino acid sequence (using single letter codes) is shown above the DNA sequence, with the start codon and signal peptide shown in bold. The previously known start codon is underlined (Met-39). FIG. 4A depicts a diagrammatic representation of SPOC-I, while FIG. 4B depicts the prior art truncated OC-I gene construct. In FIG. 4A, pSPOC-I contains the complete OC-I coding sequence, including the signal peptide, between the cauliflower mosaic virus 355 promoter and NO5 3' termination of pBGG-2. In FIG. 4B, pOC-I contains the truncated OC-I coding sequence that lacks 114 bp and does not code for the OC-I signal peptide. The arrow on FIG. 4A indicates the coding region not represented by the truncated OC-I of FIG. 4B, which lacks approximately twelve amino acids. These amino acids are believed to exist on OC-I after processing of SPOC-I in vivo.

The signal peptide sequence is amplified by PCR using genomic DNA from *O. Sativa* seedlings and ligated to the 5' end of the truncated OC-I gene at the endogenous SalI site. Partially purified protein extracts from *Escherichia coli* expressing SPOC-I react with polyclonal antibodies raised against OC-I, and express a protein of the expected and correct 15,355 Da molecular weight. In vitro translation of SPOC-I in the presence of microsomal membranes yields a processed product approximately 2.7 kDa smaller than the SPOC-I pre-protein. *Nicotiana tabacum* L. xanthi plants independently transformed with the SPOC-I gene process SPOC-I and accumulate the mature form of OC-I (approximately 12.6 kDa), which co-migrates with natural, mature OC-I extracted from rice seed when separated by SDS-PAGE.

Amplification of the CDNA sequence encoding SPOC-I using PCR allows for expression of the PCR product in *E. Coli*. Using genetic engineering techniques, the cDNA encoding SPOC-I can be transferred to plant species susceptible to either plant pests utilizing cysteine proteases, which therefore may be regulated by use of a cysteine protease inhibitor, or to viruses with processing mechanisms involving cysteine proteases, or to both.

The cDNA can be used to express large amounts of SPOC-I in various cells, including eukaryotic cells, including but not limited to bacteria and yeasts, as well as plants. For eukaryotic systems incorporating microsomal processing means, such as provided by endoplasmic reticulum, the SPOC-I is processed into OC-I of this invention, resulting in a peptide of approximately 12.6 kDa, and of the sequence SEQ ID NO: 1.

In a further embodiment of this invention, expression vectors are provided for use in transforming plants and promoting the expression of SPOC-I and OC-I in the transformed plants. Such vectors comprise the cDNA sequence of the present invention, which may be operably linked to one or more control elements, including promoters, termination sequences and various markers.

The invention includes modified SPOC-I and OC-I peptides that may be isolated or constructed through techniques known in the art. Such modified SPOC-I is characterized, in part, by having homology with at least a portion of the signal peptide portion of SPOC-I, or alteratively by incorporating a functionally similar signal peptide sequence. Such modified OC-I peptide is characterized, in part, by having homology with at least a portion of the first twelve residues of SEQ ID NO: 1, or alternatively may be characterized as resulting from processing of a pre-protein SPOC-I, or a polypeptide that is a modified SPOC-I. Modified SPOC-I and OC-I peptides are functionally equivalent to SPOC-I and OC-I of this invention, and may have substantial amino acid sequence homology, comprising at least 50% identity thereto. A functionally equivalent SPOC-I pre-protein is one wherein one or more amino acids have been added, substituted or removed without substantially reducing the pre-protein's ability to be processed into OC-I of this invention, or functionally equivalent OC-I peptide. A functionally equivalent OC-I peptide is one wherein one or more amino acids have been added, substituted or removed without substantially reducing the peptide's protease inhibitory activity as compared to OC-I of this invention. Those skilled in the art are aware that various amino acid residues may be replaced or deleted in a peptide or pre-protein, and that amino acid residues may be added to a peptide or pre-protein, and yet the resulting peptide or pre-protein maintains its function. A modified but functionally equivalent OC-I may include peptides with an even higher level of insecticidal or viricidal activity than OC-I of this invention. Each of the foregoing is functionally homologous with SPOC-I and OC-I of this invention.

The invention includes production of OC-I of this invention, and peptides functionally homologous thereto, by means of recombinant DNA techniques resulting in expression of SPOC-I and functionally homologous SPOC-I. The invention further includes host cells that have been genetically transformed with nucleic acid sequences that code for SPOC-I, modifications thereof, and pre-proteins functionally homologous with SPOC-I. Such host cells may include plant cells and bacterial cells.

It is known in the art that the degeneracy of the genetic code allows for various nucleic acid sequences to encode the same peptide sequence. When cloning SPOC-I and the OC-I peptides of this invention in a host organism, it may prove desirable to alter the nucleic acid codons such that other nucleic acid sequences are employed, which result in a SPOC-I translation product or a functionally homologous translation product. The invention includes all such synonymous and all such functionally equivalent codon sequences, resulting in a SPOC-I translation product or a functionally homologous translation product.

The invention includes nucleic acid sequences that hybridize with the cDNA SPOC-I sequence of SEQ ID NO. 3, portions thereof, and sequences that are functionally homologous therewith. The DNA to be used for hybridization may be prepared in any manner known in the art, and may be targeted to form an identifiable hybridization probe by procedures and techniques known in the art.

Vectors including the hybridization sequences are another embodiment of the invention. Expression vectors are typically plasmids. There are many types of vectors known to those of skill in the art, including virus vectors, baculovirus vectors, phage vectors and other vectors suitable for plant transformation. The insertion of the desired DNA sequences into plant or bacteria host cells according to this invention may be done by any technique or method known in the art.

Transformation, the insertion of the DNA into the host cells, may be undertaken by any of the techniques and methods known in the art. These include, but are not limited to, direct transfer of DNA into whole cells or tissues, which may include use of chemical or physical agents, as well as other means, such as electroporation and ballistic implantation of DNA-coated particles.

This invention includes transformation of plants with DNA that results in expression of SPOC-I and processing to OC-I of this invention to produce decreased susceptibility to damage by plant insect pests and other plant pests that utilize cysteine digestive proteases. Such insect pests include, but are not limited to, those insect pests that process proteins through the use of cysteine proteases in the gut. Plant pests further include nematodes and other pests the growth, survival or reproduction of which are inhibited by protease inhibitors.

This invention includes transformation of plants with DNA that results in expression of SPOC-I and processing to OC-I of this invention to produce decreased susceptibility to damage by plant viruses, particularly those plant viruses that involve cysteine proteases in processing essential for replication of the viruses. A representative example includes those in the family Potyviridae, such as in the genus Potyvirus, including but not limited to tobacco etch virus and potato virus Y. Viral families, at least some members of which are implicated in the cysteine protease processing in replication, include Potyviridae, Comoviridae, and Tymoviridae.

Plants which may be made less susceptible to damage by insect or nematode pests, and less susceptible to damage by viruses, by the practice of this invention include but are not limited to the following crop plants: maize, sweet corn, squash, melon, cucumber, sugarbeet, sunflower, rice, cotton, canola, sweet potato, bean, cowpea, tobacco, soybean and alfalfa.

A further aspect of this invention includes an insecticidal or viricidal composition including as an active ingredient an insecticidally effective amount or viricidally effective amount of OC-I of this invention. The terms "insecticidally effective amount" or "viricidally effective amount" means an amount sufficient to achieve control of an insect plant pest (including nematodes) or a plant virus, by reducing the number of insects or nematodes through mortality, reduced growth, reduced reproduction or the like, and by reducing the spread and efficacy of viruses. OC-I of this invention may be formulated in a number of ways known to those skilled in the art. Formulations may be in spray form, may contain surfactants, and may further contain other active ingredients. The formulations may be applied at any place where control is desired, and may be applied directly to plants.

Based upon the discovery of the mature form of OC-I, and the discovery of SPOC-I, together with the determination that there is a signal peptide for OC-I, as disclosed in SPOC-I and the cDNA encoding SPOC-I, it is possible that other heretofore unknown signal peptides or leader sequences, related to various plant cystatins, exist. Specifically, a putative signal peptide or leader sequence has been identified for oryzacystatin-II (OC-II), and it is hypothesized that utilization of the cDNA encoding for the signal peptide or leader sequence together with OC-II will result in enhanced expression of OC-II. A similar putative signal peptide or leader sequence has further been identified for a cystatin found in the cowpea.

Industrial Applicability:

The invention is further illustrated by the following non-limiting examples.

EXAMPLE 1

Construction of Recombinant Plasmids

The OC-I gene construct was created by ligating into pSP73 a truncated form of OC-I beginning at the previously published start site at the BamHI and KpnI sites, as shown in FIG. 1. To create SPOC-I, genomic DNA from 10 day-old *Oryza sativa* L. japonica seedlings was obtained by cetyl trimethyl ammonium bromide extraction (Richter et al., Characterization and genomic organization of a highly expressed late nodulin gene subfamily in Soybeans. *Mol Gen Genet* 229: 445–452 (1991)). The OC-I signal peptide (SP) coding region was amplified from the genomic DNA using PCR with primer sequences (restriction sites are in bold): 5'-CCC AGA TCT ATG CGG AAA TAT CGA GTC GCC-3' (sense) (SEQ ID NO: 5) and 5'-GCG AGG TCG ACG AGG TGG AGG-3' (complementary strand) (SEQ ID NO: 6). A BglII site was inserted upstream adjacent to the start codon, with complementary extension started 5 bp down from an existing SalI site. The SP fragment was ligated into pGEM-T (Promega) and sequenced using T7 Sequenase v2.0 DNA (Amersham Life Science) and LI-COR automated sequencing. The complete SPOC-I construct was created by ligation of the SP fragment (BglII, SalI), the OC-I fragment (SalI, EcoRI) cut from original OC-I cDNA provided by Abe et al. (1987, supra), which includes the 3' UTR, and pSP73 (BglII, EcoRI). Correct insertion of the fragment was confirmed by restriction digests and sequencing.

EXAMPLE 2

Translational Analysis of Recombinant Proteins

Figure 2:
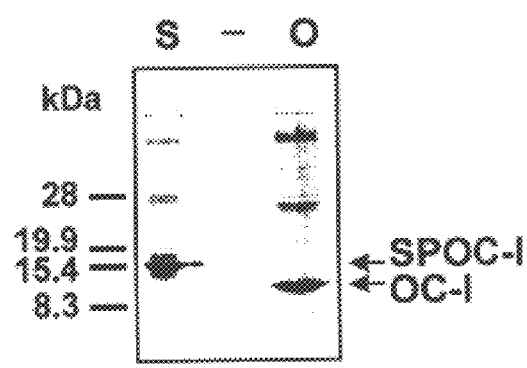
FIG. 2 is an image of soluble protein fractions of pSPOC-I-NPF$^{-OF}$ (S), pNPF$^{-OF}$ containing no insert (−) and pOC-I-NPF$^{-OF}$ (O) expressed in E. coli and electroblotted on nitrocellulose using SDS-PAGE and challenged with polyclonal antibodies raised against recombinant OC-I.

In-vitro transcription of OC-I and SPOC-I was done by standard procedures (Promega). DNA templates (5 μg) of both constructs (in pSP73) were reacted with SP6 RNA polymerase. In vitro translation and microsomal processing of OC-I and SPOC-I were performed using the rabbit reticulocyte lysate system and canine pancreatic microsomal membranes (Promega). The synthetic transcript reaction mix was labeled with $^{35}$S-methionine and separated by 16% SDS-PAGE. Autoradiography was used to detect translation products. FIG. 2 depicts the analysis of soluble protein fragments from pSPOC-I-NPF$^{-OF}$ (5), pNPF$^{-OF}$ with no insert (~), and pOC-I-NPF$^{-OF}$ (O) expressed in *E. coli*. 2 mg of PBS-soluble protein extract were separated by SDS-PAGE and electroblotted to nitrocellulose. The blot was incubated with polyclonal antibodies against recombinant OC-I, goat ant-rabbit IgG-alkaline phosphatase and reacted as described. Arrows indicate the SPOC-I and OC-I proteins. The molecular masses are indicated on the left of the panel.

EXAMPLE 3

Expression of Recombinant Proteins in *E. coli*

The OC-I and SPOC-I fragments were ligated into the BamHI/KpnI and BglII/EcoRI sites of a pFLAG expression vector (IBI Kodak), modified to omit the OmpA signal peptide and FLAG peptide coding regions (pNPF$^{-OF}$). These plasmids, pSPOC-I-NPF$^{-OF}$ and pOC-I-NPF$^{-OF}$, were then transformed into *E. coli* DH5α competent cells. Transformed cultures were induced for two hours with isopropyl b-D-thiogalactopyranoside (IPTG) for expression of the insert and subjected to 3 freeze-thaw cycles to release the recombinant proteins. Debris was removed by centrifugation. Total proteins were precipitated using ammonium sulfate (50–75% saturation). Soluble proteins were resuspended in phosphate buffered saline (PBS, pH 7.4), dialyzed against the same buffer, then quantitated by the Lowry method ($A_{595}$) for western analysis. The in-frame insertions of OC-I and SPOC-I into pFLAG add six additional amino acids to the NH$_2$-end of both proteins due to the modified multiple cloning site of the vector.

EXAMPLE 4

Tobacco Transformation and Tissue Culture

The SPOC-I fragment was ligated into pBGG-2, a modified pMON316 vector, and introduced into *E. coli* DH5α competent cells. The vector was introduced into *Agrobacterium tumefaciens* strain pTiT37SE by tri-parental mating with the helper strain, pRK2013 (Rogers et al., Improved vectors for plant transformation: expression cassette vectors and new identifiable markers. *Methods and Enzymology* 153: 253–263 (1987)). *Nicotiana tabacum* L. xanthi was transformed using the *A. tumefaciens* as previously described (Horsch et al., A simple and general method for transforming genes into plants. *Science* 227: 1229–1231 (1985)). Transformants were selected and regenerated on Murashige and Skoog medium containing antibiotics and growth hormones.

EXAMPLE 5

Plant Protein Extracts

Leaves from *N. tabacum* plants and immature rice seeds from non-transformed *O. sativa* were collected and ground in PBS, pH 7.4. The protein extract was collected by centrifugation and incubated at 70° C. for 10 minutes. The soluble protein fraction was quantified by the Lowry method and precipitated with ethanol.

EXAMPLE 6

SDS-PAGE and Western Blot Analysis

Figure 3:
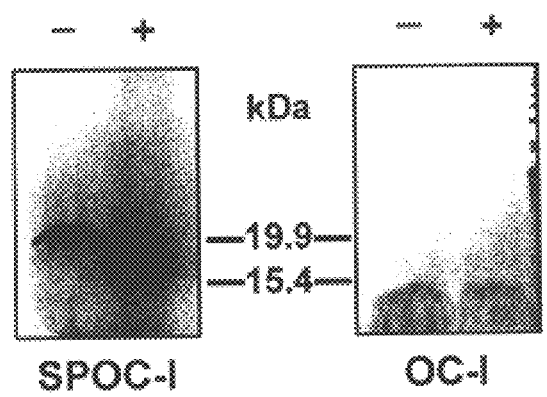
FIG. 3 depicts two images of autoradiographs obtained using SDS-PAGE of in vitro translation products from in vitro transcribed SPOC-I and OC-I in the absence (−) and presence (−) of microsomes.

Proteins were separated by 16% SDS-PAGE and electroblotted onto nitrocellulose (Laemmli, Cleavage of structural proteins during the assembly of the head of bacteriophage $T_4$. *Nature* 227: 680–685 (1970)). After blocking, the blots were incubated with polyclonal antibodies raised against recombinant OC-I. The blots were incubated with goat anti-rabbit IgG-alkaline phosphatase (Southern Biotechnology Associates) and reacted with alkaline phosphatase buffer containing nitro blue tetrazolium and 5-bromo-4-chloro-3-indolyl phosphate according to manufacturer (Promega). FIG. 3 depicts autoradiographs of the in vitro translation products from in vitro transcribed SPOC-I and OC-I in the absence (−) and presence (+) of microsomes. Loading buffer was added to one-tenth of each reaction (consisting of 2 mg synthetic transcript labeled with 35S-methiorine) before separating by SDS-PAGE. The molecular masses are indicated between the two panels of FIG. 3.

EXAMPLE 7

Bioinformatics

Analysis of the 5'-end of the OC-I gene reveals that translation from an ATG putative start site (Met-1, FIG. 1) upstream of that previously published produces a peptide containing a leader sequence that is highly homologous to N-terminal leader sequences found in corn cystatin-I and -II (CC-I and CC-II) as well as sorghum cystatin (SC). The leader regions for CC-I and CC-II share 78% and 70% conserved amino acids with the putative OC-I signal peptide, respectively, while the leader region from SC shares 62% homology (SwissProt database). Computational analyses of the OC-I leader sequence using PSORT and PC Gene (IntelliGenetics, Inc.) indicate that the cleavage of the putative pre-protein occurs at Ala-26 and that the mature OC-I protein beginning at Glu-27 is destined for the vesicular pathway, a reasonable destiny given its natural accumulation in rice seed during the several weeks after flowering. In addition, processing of the corn cystatin signal peptides is predicted to occur at similar locations, just outside the hydrophobic regions which share conserved residues with the OC-I leader sequence. Also corroborating the predicted proteolytic site within the putative leader sequence of OC-I is a signal peptide within the human cystatin C pre-protein: it is also processed at the 26-amino acid position (Abrahamson et al., Molecular cloning and sequence analysis of cDNA coding for the precursor of the human cysteine proteinase inhibitor cystatin C. *FEBS Lett* 216(2): 229–233 (1987)) and shares conserved residues with the OC-I signal peptide.

EXAMPLE 8

Microsomal Processing of SPOC-I

Figure 5:
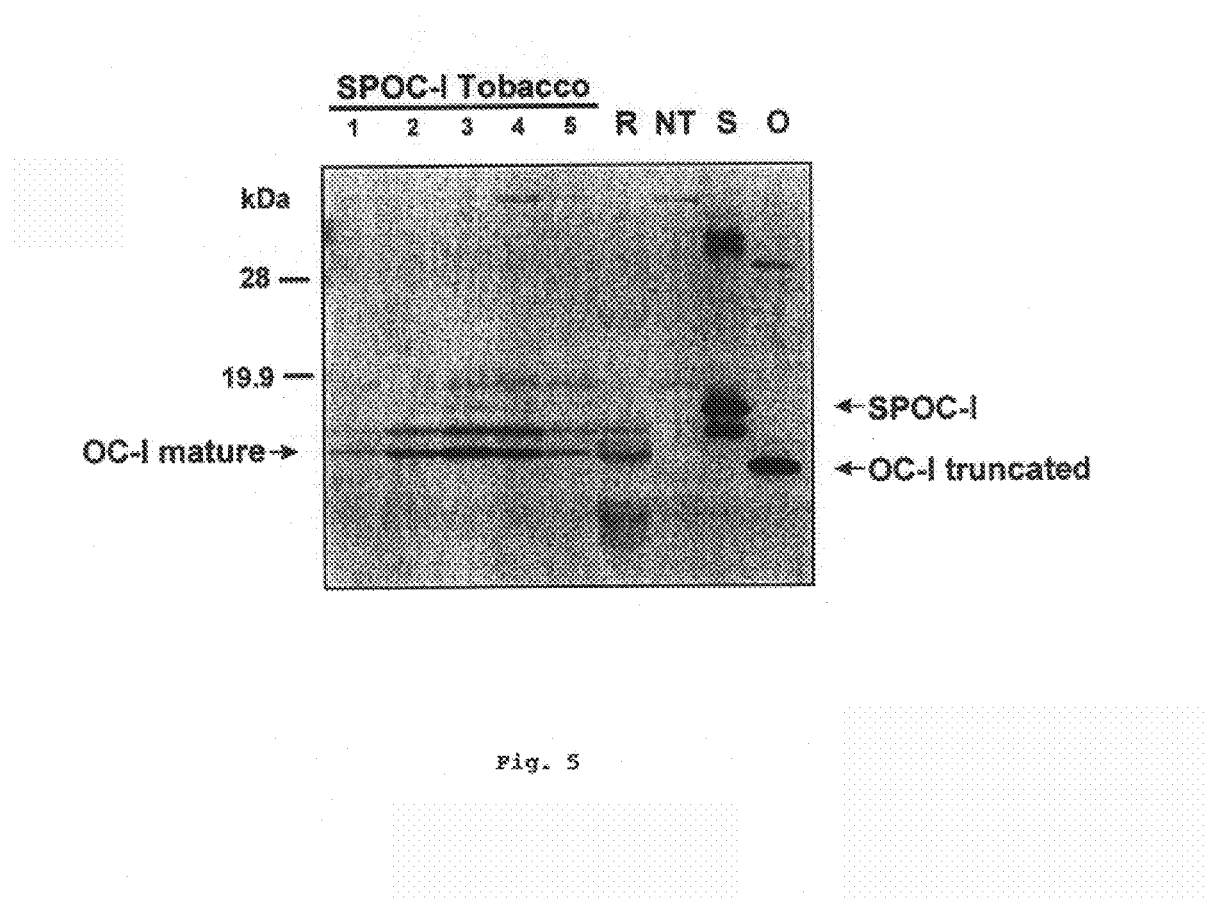
FIG. 5 is an image of soluble protein fractions from tobacco independently transformed with SPOC-I (1–5), non-transformed tobacco (NT), non-transformed immature rice seed (R), E. Coli-expressed SPOC-I (S) and truncated OC-I (O), electroblotted on nitrocellulose using SDS-PAGE and challenged with polyclonal antibodies raised against recombinant OC-I. Molecular masses are indicated on the left of the panel.

To investigate the function of the putative OC-I signal peptide, transcribed mRNA from SPOC-I and OC-I was translated in vitro. In the absence of microsomes, unprocessed polypeptides are produced from SPOC-I and OC-I mRNA. In the presence of microsomes, however, SPOC-I is processed into a peptide approximately 2.7 kDa smaller, whereas no processing is observed for the truncated OC-I. The processed OC-I, which may represent the mature form of OC-I produced in rice, is about 1.5 kDa larger than the truncated protein. These data indicate that the signal peptide is recognized and processed by the microsomal membranes, suggesting that in vivo SPOC-I is targeted to the endoplasmic reticulum. FIG. 5 is an image of soluble protein fractions from tobacco independently transformed with SPOC-I (1–5), non-transformed tobacco (NT), non-transformed immature rice seed (R), *E. Coli*-expressed SPOC-I (S) and truncated OC-I (O), electroblotted on nitrocellulose using SDS-PAGE and challenged with polyclonal antibodies raised against recombinant OC-I. Molecular masses are indicated on the left of the panel. One hundred mg of PBS-soluble protein from each sample was separated by SDS-PAGE and electroblotted. The blot was incubated with polyclonal antibodies against recombinant OC-I and processed as described in Example 6.

EXAMPLE 9

Western Analysis of OC-I Protein

The soluble protein fraction induced in *E. coli* contained polypeptides that reacted with polyclonal antibodies raised against OC-I. The molecular weight.(MW) of these proteins was approximately 15.3 kDa, the estimated MW of the SPOC-I pre-protein before processing with six additional amino acids, and 12.2 kDa, the estimated MW of truncated OC-I plus six amino acids.

To determine whether SPOC-I is biologically active in vivo, SPOC-I was placed under the constitutive control of the CaMV-35S promoter (FIG. 1B) and transformed *N. tabacum* via *A. tumefaciens*. Western analysis demonstrates that the SPOC-I pre-protein produced in independently transformed tobacco is processed and co-migrates with the natural, mature OC-I obtained from rice, as shown in FIG. 2. As predicted, the mature OC-I in both tobacco and rice is approximately 12.6 kDa and slightly larger than the truncated OC-I produced in *E. coli*, indicating the predicted proteolytic site is at or very near the Ala-26 position. A second product of approximately 14.4 kDa is also observed in both transgenic tobacco and non-transformed rice. The second protein product may be the result of an additional processing site, or post-translational modification (Chrispeels, Sorting of proteins in the secretory system. *Annu Rev Plant Physiol Plant Mol Biol* 42: 21–53 (1991); Ahman et al., Sequence analysis and regulation of a gene encoding a cuticle-de grading serine protease from the nematophagus fungus *Arthrobotrys oligospor. Microbiology* 142: 1605–1616 (1996)).

EXAMPLE 10

Expression of OC-I from Tobacco

Tobacco plants were transformed with SPOC-I of this invention as described in Example 4, while other tobacco plants were transformed with prior art truncated OC-I. Semi-quantitative analysis showed expression of the mature form of OC-I in plants transformed with SPOC-I of this invention, of the same molecular weight as OC-I expressed natively in non-transformed immature rice seed. Tobacco plants transformed with prior art truncated OC-I showed much lower expression of truncated, lower molecular weight OC-I, compared to expression of OC-I in SPOC-I transformed plants with a lower molecular weight.

EXAMPLE 11

Topical use of OC-I as Insecticide

OC-I is made utilizing a nucleic acid sequence encoding an amino acid sequence including both a signal peptide for OC-I and an OC-I peptide expressed in any eukaryotic cell system, the resulting amino acid sequence is then processed utilizing microsomes or other suitable means, and the processed OC-I is recovered, and is characterized by being approximately 12.6 kDa MW. The resulting OC-I is mixed with one or more agriculturally acceptable carriers, and applied as a spray, dust, pellet, aerosol or by other means known in the art, in an effective amount, and is further applied directly to the insect pest, or alternatively to plants, including crop plants, on which such insect pest feeds.

EXAMPLE 12

OC-I Transformed Plants with Insecticidal Properties

Any of a variety of food or crop plants, including but not limited to maize, sweet corn, squash, melon, cucumber, sugarbeet, sunflower, rice, cotton, canola, sweet potato, bean, cowpea, tobacco, soybean and alfalfa, may be transformed utilizing a vector which encodes an amino acid sequence including both a signal peptide for OC-I and an OC-I peptide. Such vectors include those described in Example 4 above, and other vectors which may be utilized by those skilled in the art. Other means of genetic transformation of plants may also be employed, including those described in U.S. Pat. Nos. 5,990,390 and 6,013,863. Depending on the means of transformation employed, the resulting transgenic plants may be fertile, and may transmit expression of OC-I peptide to progeny plants through normal sexual cycles. Such plants may naturally express OC-I, as in the case of rice, wherein the genetic transformation increases the expression of OC-I. The genetically transformed plants express effective quantities of OC-I peptide, which has an insecticidal effect on certain plant pests, including specifically those plant pests susceptible to digestive system cysteine protease inhibitors, such as Coleoptera and nematodes.

EXAMPLE 13

OC-I Transformed Plants with Viricidal Properties

Any of the plants and methods of Example 11 above may be employed, resulting in genetically transformed plants that express effective quantities of OC-I peptide, which has a viricidal effect on certain certain viruses, including potyviruses, that involve the activity of cysteine proteinases. The viruses may include tobacco etch virus and potato virus Y.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An oryzacystatin-I protease inhibitor peptide comprising the amino acid sequence of SEQ ID NO: 1.

2. An isolated pre-oryzacystatin-I peptide denominated SPOC-I characterized by the amino acid sequence of SEQ ID NO: 4.

3. A transgenic plant comprising a foreign nucleic acid sequence encoding the peptide according to claim 2.

4. A transgenic plant comprising a foreign nucleic acid sequence encoding both a signal peptide for OC-I and an OC-I peptide.

5. Protein derived from the expression of a nucleic acid sequence encoding both a signal peptide for OC-1 and an OC-1 peptide.

6. A cystatin protease inhibitor peptide having an amino acid sequence extending from amino acid position 13 to amino acid position 37 of SEQ ID NO: 1 and at least a portion of the sequence extending from amino acid position 1 to amino acid position 12.

7. A transgenic plant comprising a foreign nucleic acid sequence encoding the peptide according to claim 6.

8. A homogenous protease inhibitor OC-I peptide characterized by a molecular weight of at least about 12.6 kDa on an SDS PAGE with binding affinity to polyclonal antibodies to recombinant OC-I.

9. A method of combating insect pests which comprises exposing said pests to an insecticidally effective amount of an OC-I peptide wherein said peptide is expressed in a plant or plant colonizing microorgranism as a result of genetic transformation by a nucleic acid sequence encoding both a signal peptide for OC-I and an OC-I peptide.

10. The method of claim 9 wherein the plant is a maize, sweet corn, squash, melon, cucumber, sugarbeet, sunflower, rice, cotton, canola, sweet potato, bean, cowpea, tobacco, soybean or, alfalfa plant.

11. A method of combating viruses with processing mechanisms involving cysteine proteases, which method comprises exposing said viruses to a viricidally effective amount of an OC-I peptide wherein said peptide is expressed in a plant as a result of genetic transformation by a nucleic acid sequence encoding both a signal peptide for OC-I and an OC-I peptide.

12. The method of claim 11 wherein the plant is a maize, sweet corn, squash, melon, cucumber, sugarbeet, sunflower, rice, cotton, canola, sweet potato, bean, cowpea, tobacco, soybean or alfalfa plant.

* * * * *